(12) United States Patent
Tsunoi et al.

(10) Patent No.: US 10,971,029 B2
(45) Date of Patent: Apr. 6, 2021

(54) INFORMATION PROCESSING DEVICE, METHOD, AND STORAGE MEDIUM

(71) Applicant: KABUSHIKI KAISHA TOSHIBA, Tokyo (JP)

(72) Inventors: Yasuyuki Tsunoi, Saitama (JP); Kazunori Imoto, Kanagawa (JP); Kanako Nakayama, Tokyo (JP); Sawa Fuke, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 282 days.

(21) Appl. No.: 15/906,828

(22) Filed: Feb. 27, 2018

(65) Prior Publication Data

US 2019/0019431 A1 Jan. 17, 2019

(30) Foreign Application Priority Data

Jul. 13, 2017 (JP) ............................. JP2017-137258

(51) Int. Cl.
| | |
|---|---|
| *G09B 19/00* | (2006.01) |
| *G06Q 50/20* | (2012.01) |
| *A61B 5/0488* | (2006.01) |
| *G09B 19/24* | (2006.01) |
| *A61B 5/11* | (2006.01) |
| *G09B 5/02* | (2006.01) |
| *A61B 5/00* | (2006.01) |

(52) U.S. Cl.
CPC .......... *G09B 19/003* (2013.01); *A61B 5/0488* (2013.01); *A61B 5/1114* (2013.01); *A61B 5/6842* (2013.01); *G06Q 50/2057* (2013.01); *G09B 5/02* (2013.01); *G09B 19/24* (2013.01)

(58) Field of Classification Search
CPC .............................. G09B 19/00; G09B 19/003
USPC ....... 434/219, 236, 247, 248, 250, 252, 258; 340/573.1, 573.7; 700/91
See application file for complete search history.

(56) References Cited

U.S. PATENT DOCUMENTS 5,372,365 A * 12/1994 McTeigue .......... A63B 24/0003
434/252
5,679,004 A * 10/1997 McGowan ............. A63B 69/00
434/247

(Continued)

FOREIGN PATENT DOCUMENTS

| JP | 2001-71140 A | 3/2001 |
|---|---|---|
| JP | 2001-166680 A | 6/2001 |

(Continued)

*Primary Examiner* — Kurt Fernstrom
(74) *Attorney, Agent, or Firm* — Finnegan, Henderson, Farabow, Garrett & Dunner, L.L.P.

(57) ABSTRACT

According to one embodiment, an information processing device includes a memory and a hardware processor in communication with the memory. The hardware processor is configured to acquire a first motion data indicating a motion of a first operator, acquire a second motion data indicating a motion of a second operator, compare the first motion data and the second motion data, determine a similarity of the first motion data and the second motion data, and present to the first operator instruction data indicating an improvement point relating to a motion at a time of performing a predetermined operation in accordance with a determination result.

20 Claims, 10 Drawing Sheets

(56) References Cited

U.S. PATENT DOCUMENTS

| | | | | |
|---|---|---|---|---|
| 5,947,742 | A * | 9/1999 | Katayama | A63B 24/0003 434/247 |
| 6,293,802 | B1 * | 9/2001 | Ahlgren | A63B 24/0003 434/252 |
| 8,159,354 | B2 * | 4/2012 | Ferguson | A63F 13/211 340/12.22 |
| 8,579,632 | B2 * | 11/2013 | Crowley | G06Q 30/02 434/247 |
| 8,953,909 | B2 * | 2/2015 | Guckenberger | G06T 11/00 382/305 |
| 2003/0054327 | A1 * | 3/2003 | Evensen | A63B 24/0003 434/252 |
| 2009/0253109 | A1 * | 10/2009 | Anvari | G09B 23/28 434/262 |
| 2010/0221695 | A1 * | 9/2010 | Desai | G09B 7/02 434/428 |
| 2011/0276153 | A1 * | 11/2011 | Selner | A63B 69/3623 700/91 |
| 2013/0244211 | A1 * | 9/2013 | Dowling | G06F 19/3481 434/247 |
| 2013/0302768 | A1 * | 11/2013 | Webb | G09B 19/0038 434/247 |
| 2014/0113262 | A1 * | 4/2014 | Kostuj | A63B 60/46 434/252 |
| 2014/0199672 | A1 * | 7/2014 | Davidson | A63B 69/00 434/247 |
| 2014/0234814 | A1 * | 8/2014 | Krosky | A63B 24/0075 434/236 |
| 2015/0125835 | A1 * | 5/2015 | Wittich | A63H 33/042 434/169 |
| 2016/0045170 | A1 * | 2/2016 | Migita | A61B 5/743 434/247 |
| 2016/0049089 | A1 * | 2/2016 | Witt | G09B 19/0038 434/258 |
| 2016/0086500 | A1 * | 3/2016 | Kaleal, III | G06T 19/00 434/257 |
| 2016/0101318 | A1 * | 4/2016 | Kito | G06K 9/00536 434/258 |
| 2016/0140867 | A1 * | 5/2016 | Aragones | G06F 19/3481 434/257 |
| 2016/0148534 | A1 * | 5/2016 | Howell | G09B 19/0038 434/257 |
| 2016/0180059 | A1 * | 6/2016 | Kuo | G06F 19/3481 434/247 |
| 2016/0192866 | A1 * | 7/2016 | Norstrom | A61B 5/1123 434/247 |
| 2016/0196758 | A1 * | 7/2016 | Causevic | G09B 5/00 434/236 |
| 2016/0199719 | A1 * | 7/2016 | Winsper | G09B 19/0038 434/247 |

FOREIGN PATENT DOCUMENTS

| | | |
|---|---|---|
| JP | 2001-166681 | 6/2001 |
| JP | 2005-134536 A | 5/2005 |
| JP | 2006-171184 | 6/2006 |
| JP | 2011-164694 A | 8/2011 |
| JP | 2013-88730 A | 5/2013 |
| JP | 2017-64095 | 4/2017 |

* cited by examiner

| Concomitant data | | Determination result data | Character string data | |
|---|---|---|---|---|
| Sensor type | Device attachment body part | | | |
| Myoelectric sensor | Right hand | Amplitude is small | Apply strength with your right hand | ~a1 |
| Myoelectric sensor | Right hand | Amplitude is large | Release strength with your right hand | ~a2 |
| Myoelectric sensor | Right hand | Timing is slow | Hasten to apply strength with your right hand | ~a3 |
| Myoelectric sensor | Right hand | Timing is early | Slow down applying strength with your right hand | ~a4 |
| ⋮ | ⋮ | ⋮ | ⋮ | |

FIG. 7

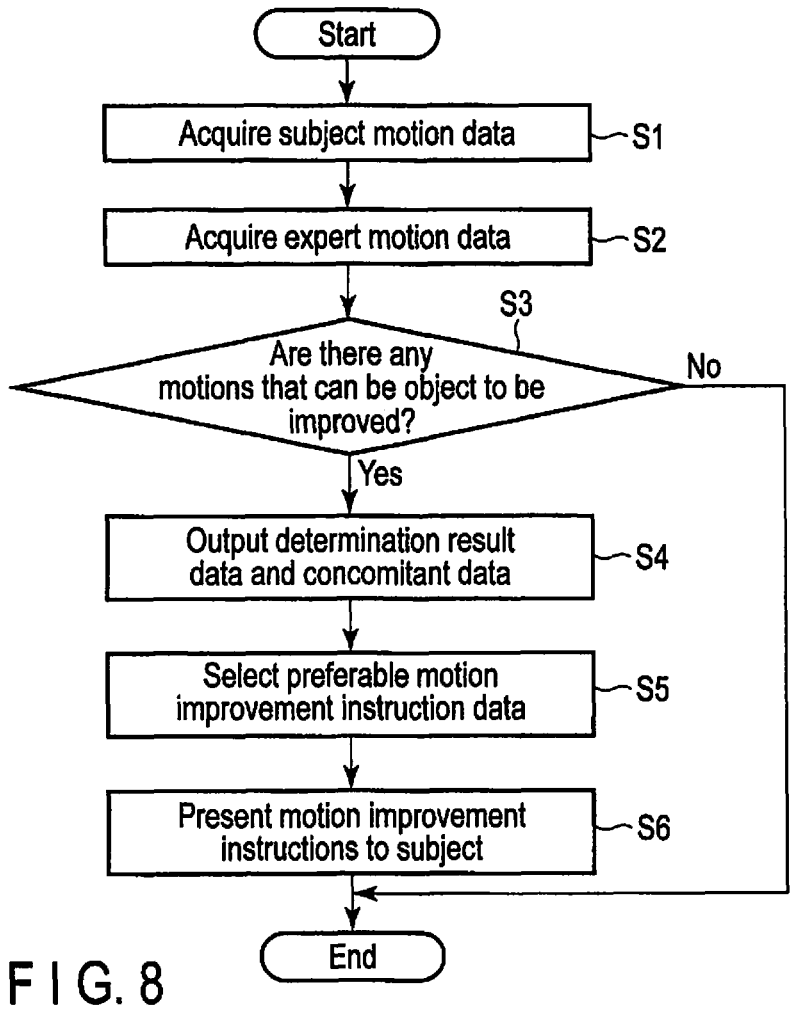

FIG. 8

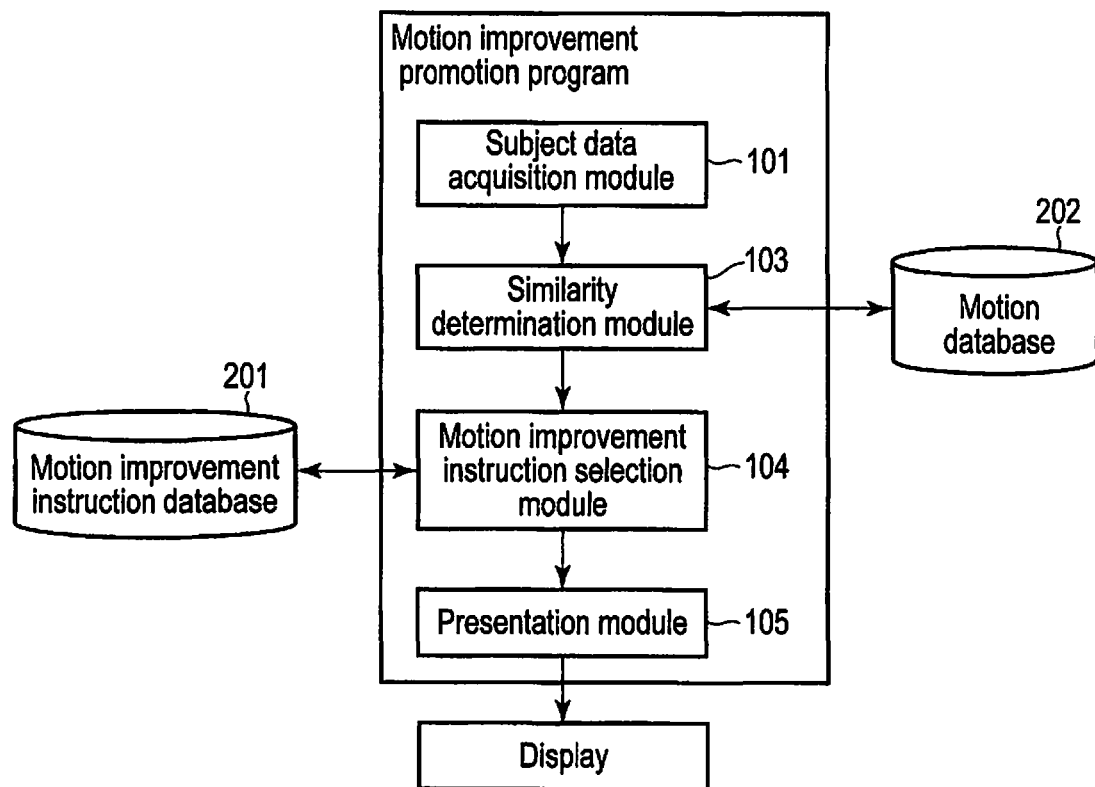

FIG. 9

| Concomitant data ||| Expert motion data |
|---|---|---|---|
| Sensor type | Attachment body part | Operation content | |
| Myoelectric sensor | Right hand | Screw tightening | Expert motion data 1 |
| Myoelectric sensor | Left hand | Screw tightening | Expert motion data 2 |
| Myoelectric sensor | Abdomen | Screw tightening | Expert motion data 3 |
| Pressure sensor | Used tool | Screw tightening | Expert motion data 4 |
| ⋮ | ⋮ | ⋮ | ⋮ |

FIG. 10

| Concomitant data | | | Expert motion data | Proficiency level data | |
|---|---|---|---|---|---|
| Sensor type | Attachment body part | Operation content | | | |
| Myoelectric sensor | Right hand | Screw tightening | 3 | Proficiency level data 1a | c1 |
| Myoelectric sensor | Right hand | Screw tightening | 2 | Proficiency level data 1b | c2 |
| Myoelectric sensor | Left hand | Screw tightening | 3 | Proficiency level data 2a | c3 |
| Myoelectric sensor | Left hand | Screw tightening | 2 | Proficiency level data 2b | c4 |
| ⋮ | ⋮ | ⋮ | ⋮ | ⋮ | |

FIG. 11

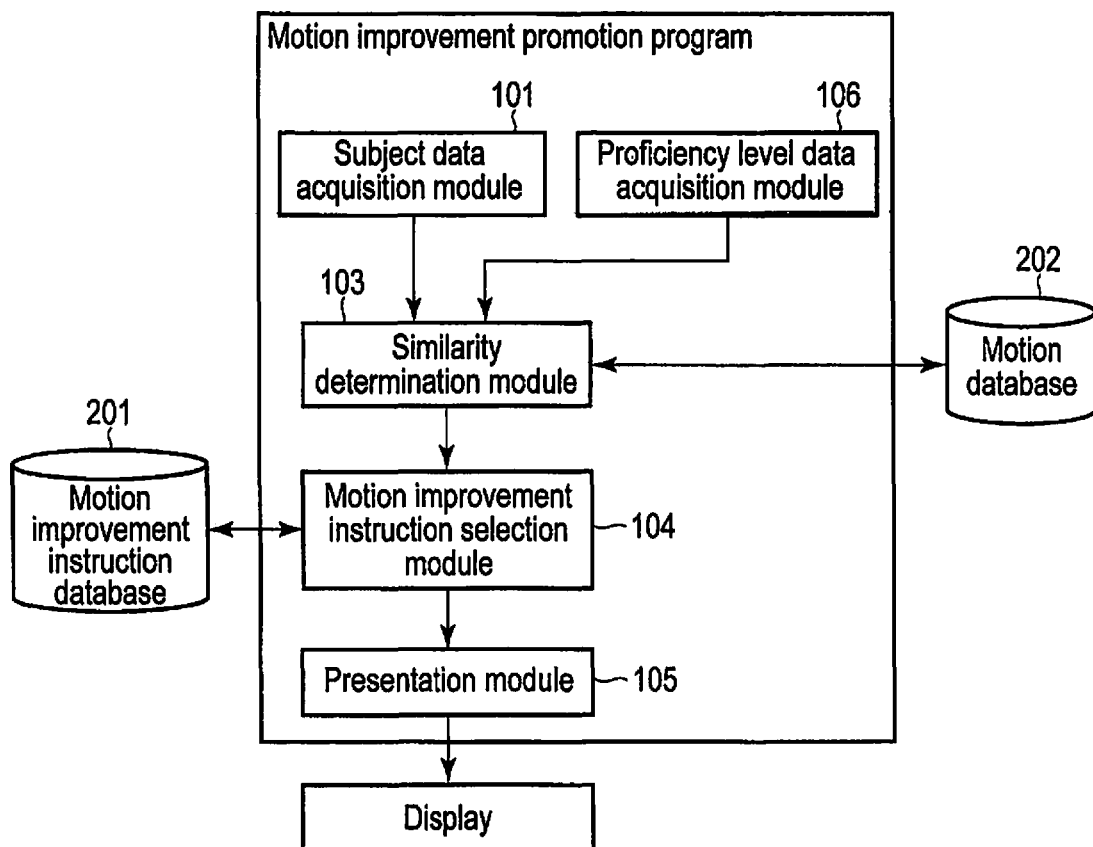

FIG. 12

| Concomitant data | | Determination result data | Estimation result data | Adverb expression | |
|---|---|---|---|---|---|
| Sensor type | Attachment body part | | | | |
| Myoelectric sensor | Right hand | Amplitude is small | Grasp | Strongly | ~d1 |
| Myoelectric sensor | Right hand | Timing is early | Twist | Slowly | ~d2 |
| ⋮ | ⋮ | ⋮ | ⋮ | ⋮ | |

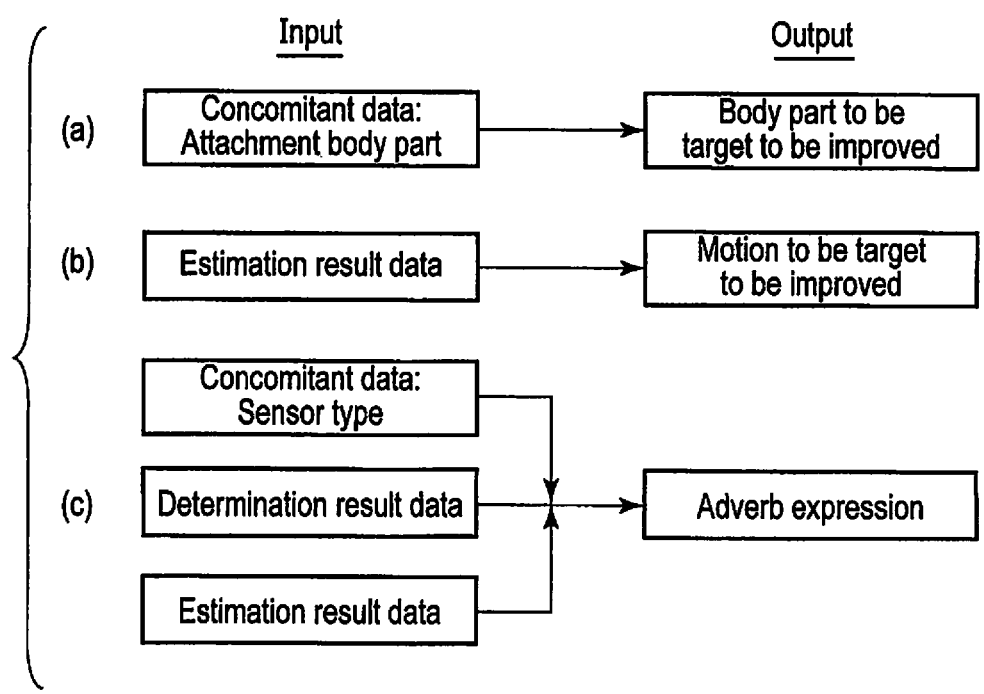
F I G. 18

INFORMATION PROCESSING DEVICE, METHOD, AND STORAGE MEDIUM

CROSS-REFERENCE TO RELATED APPLICATIONS

This application is based upon and claims the benefit of priority from Japanese Patent Application No. 2017-137258, filed Jul. 13, 2017, the entire contents of which are incorporated herein by reference.

FIELD

Embodiments described herein relate generally to an information processing device, a method, and a storage medium.

BACKGROUND

Generally, training, education and guidance to make operators acquire necessary skills at the work site are indispensable to ensure productivity. Moreover, it is important to train operators with less practical experience with less time and send them to the work site against the background of the rapid personnel transition, which is attributed to overseas facility expansion and employment of foreigners due to recent labor market mobility and globalization. For this reason, a technique capable of efficiently promoting training of operators is desired.

BRIEF DESCRIPTION OF THE DRAWINGS

FIG. 7 shows an example of a data structure of motion improvement instruction data according to the above embodiment.

FIG. 8 is a flowchart showing an example of motion improvement promotion processing according to the above embodiment.

FIG. 9 is a block diagram showing an example of a functional configuration of a motion improvement promotion program different from that in FIG. 3.

FIG. 10 shows an example of a data structure of motion data according to the above embodiment.

FIG. 11 shows an example of a data structure of motion data different from that in FIG. 10.

FIG. 12 is a block diagram showing an example of a functional configuration of a motion improvement promotion program different from that in FIG. 9.

FIG. 18 is a diagram for explaining the generation of the motion improvement instruction according to the above embodiment.

DETAILED DESCRIPTION

In general, according to one embodiment, an information processing device includes a memory and a hardware processor in communication with the memory. The hardware processor is configured to acquire a first motion data indicating a motion of a first operator, acquire a second motion data indicating a motion of a second operator, compare the first motion data and the second motion data, determine a similarity of the first motion data and the second motion data, and present to the first operator instruction data indicating an improvement point relating to a motion at a time of performing a predetermined operation in accordance with a determination result.

Hereinafter, embodiments will be described with reference to the drawings.

Figure 1:
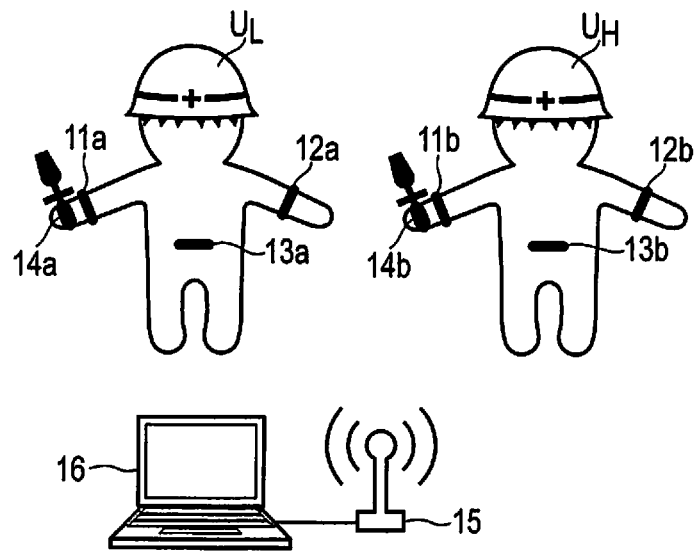
FIG. 1 is a diagram showing a schematic configuration example of a motion improvement promotion system including the information processing device according to a first embodiment.

FIG. 1 is a diagram showing a schematic configuration example of a motion improvement promotion system including the information processing device according to a first embodiment. The motion improvement promotion system shown in FIG. 1 includes a plurality of sensor devices 11 to 14, a data transceiver 15, and an information processing device 16.

The plurality of sensor devices 11 to 14 are sensors capable of measuring motion data concerning a motion when a person (user) performs a predetermined operation, and include, for example, an wearable sensor 11 to 13 in which an acceleration sensor, a gyro sensor, a geomagnetic sensor, and an myoelectric sensor are integrated, a pressure sensor 14, and the like. The sensor devices 11 to 14 are attached to a person who performs a predetermined operation, a tool used by the person to perform the predetermined operation, and the like. Various motion data measured by each of the sensor devices 11 to 14 together with concomitant data indicating the type (sensor type) of a sensor that has acquired the motion data and the body part (attachment body part, measurement body part) to which the sensor is attached is transmitted to the information processing device 16 via the data transceiver 15. Note that the concomitant data is set by, for example, the wearer (user) when the sensor devices 11 to 14 are attached.

The sensor device is not limited to the above-described wearable sensors 11 to 13 and the pressure sensor 14, but any sensor can be used as a sensor device as long as it can measure motion data concerning the operation of a person performing a predetermined operation. For example, an imaging device (camera) capable of continuously photographing the transition of a motion of a person performing a predetermined operation may be used as a further sensor device or as a sensor device replacing the sensor devices 11 to 14.

In the present embodiment, as shown in FIG. 1, suppose each of the sensor devices 11 to 13 is attached to a person (hereinafter referred to as "subject") $U_L$ having a low proficiency level with respect to a predetermined operation and a person (hereinafter referred to as "expert") $U_H$ having a high proficiency level with respect to a predetermined operation on the right hand (right arm), the left hand (left arm), and the abdomen, and the sensor device 14 is attached to a tool used by the subject $U_L$ and the expert $U_H$. Further, in the present embodiment, suppose the above-described predetermined operation is an operation of "screw tightening". However, the attachment body part to which the sensor devices 11 to 14 are attached and the content of the predetermined operation are not limited to what is mentioned in the above.

The information processing device 16 acquires the motion data of the subject (hereinafter referred to as "subject motion data") and the motion data of the expert (hereinafter referred to as "expert motion data") which are measured by the respective sensor devices 11 to 14 through the data transceiver 15. The information processing device 16 determines and selects matters to be done in order to enhance the proficiency level of the predetermined operation based on the subject motion data and the expert motion data, and performs motion improvement promotion processing in which the results are presented to the subject $U_L$ as a motion improvement instruction. The subject motion data and the expert motion data may be raw motion data measured by each of the sensor devices 11 to 14 or motion data processed on raw motion data.

Figure 2:
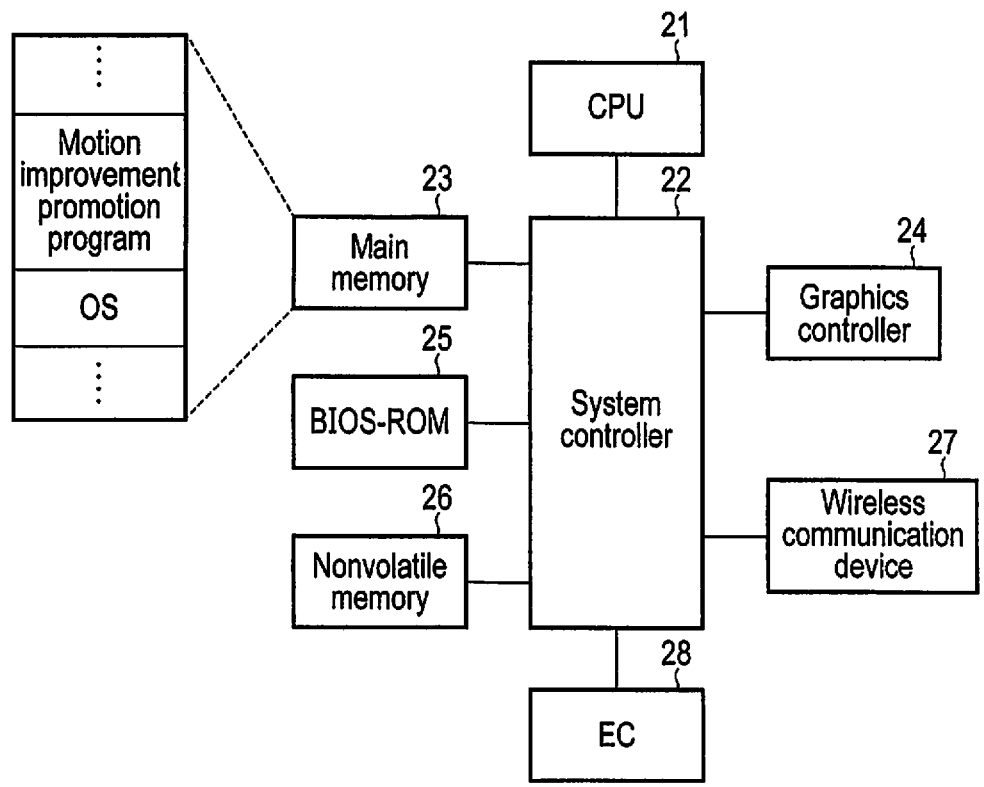
FIG. 2 is a block diagram showing an example of a hardware configuration of the information processing device according to the above embodiment.

FIG. 2 is a block diagram showing an example of a hardware configuration of the information processing device 16.

As shown in FIG. 2, the information processing device 16 includes a CPU 21, a system controller 22, a main memory 23, a graphics controller 24, a BIOS-ROM 25, a nonvolatile memory 26, a wireless communication device 27, an embedded controller (EC) 28 and the like. For example, a personal computer (PC) or the like corresponds to this information processing device 16. In the present embodiment, the description is made supposing the information processing device 16 is a PC. However, the information processing device 16 is not limited to the PC. The information processing device 16 may be a tablet computer, a smartphone, various wearable devices, or the like.

The CPU 21 is a processor (hardware processor) that controls the operation of various modules in the information processing device 16. The CPU 21 executes various software loaded from the nonvolatile memory 26 into the main memory 23. These software programs include an operating system (OS) and various application programs. The application program includes a motion improvement promotion program, and by executing the motion improvement promotion program by the CPU 21, the motion improvement promotion processing described above is realized.

The CPU 21 also executes the basic input/output system (BIOS) stored in the BIOS-ROM 25. The BIOS is a program for hardware control.

The system controller 22 is a device for connecting between the local bus of the CPU 21 and various components. The system controller 22 also incorporates a memory controller for an access control of the main memory 23. In addition, the system controller 22 also has a function of communicating with the graphics controller 24 via a serial bus or the like of the PCI EXPRESS standard.

The graphics controller 24 is a display controller that controls a display monitor (LCD) provided in the information processing device 16 and a display monitor connected to the information processing device 16.

The wireless communication device 27 is a device configured to execute wireless communication such as wireless LAN or 3G/4G mobile communication. The EC 28 is a one-chip microcomputer including an embedded controller for power management, and has a function of performing power-on/power-off of the information processing device 16 in response to user's operation.

Figure 3:
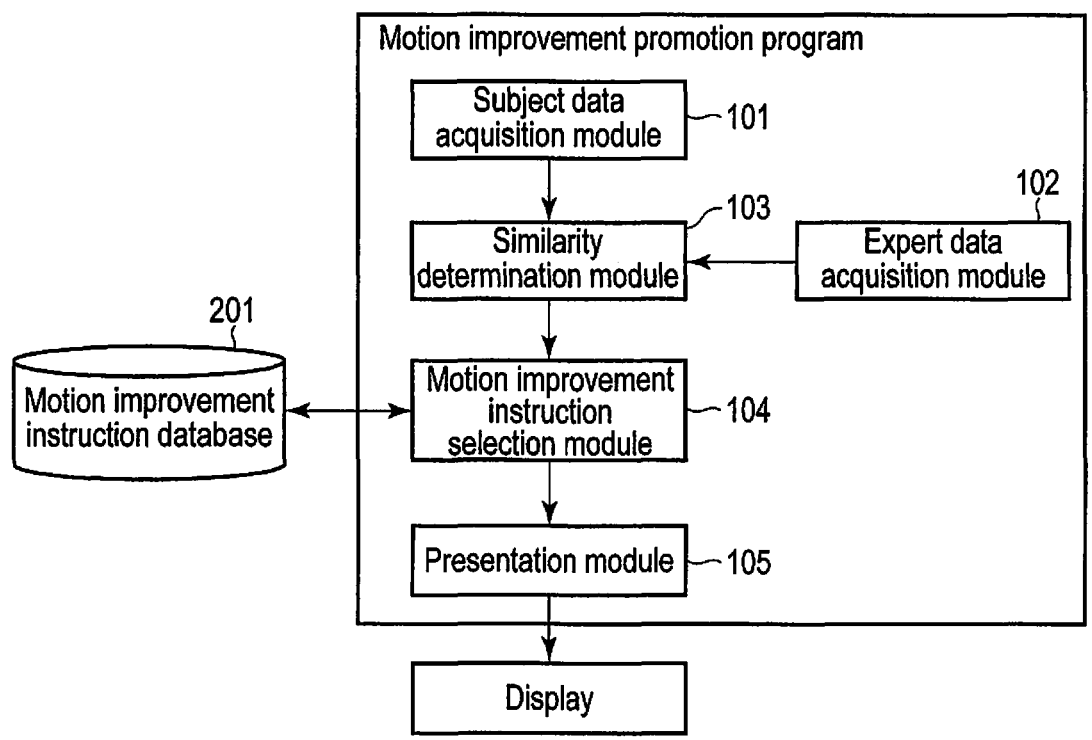
FIG. 3 is a block diagram showing an example of the functional configuration of the motion improvement promotion program executed by the information processing device according to the above embodiment.

FIG. 3 is a block diagram showing an example of a functional configuration of the motion improvement promotion program.

The motion improvement promotion program includes a subject data acquisition module 101, an expert data acquisition module 102, a similarity determination module 103, a motion improvement instruction selection module 104, a presentation module 105, and the like as a function module. In the following, each function module 101 to 105 will be described in detail, and the motion improvement instruction database 201 will be described in detail. The motion improvement instruction database 201 includes a storage device in the information processing device 16, a storage device externally attached to the information processing device 16, a server device on the cloud providing storage services, or the like.

Figure 4:
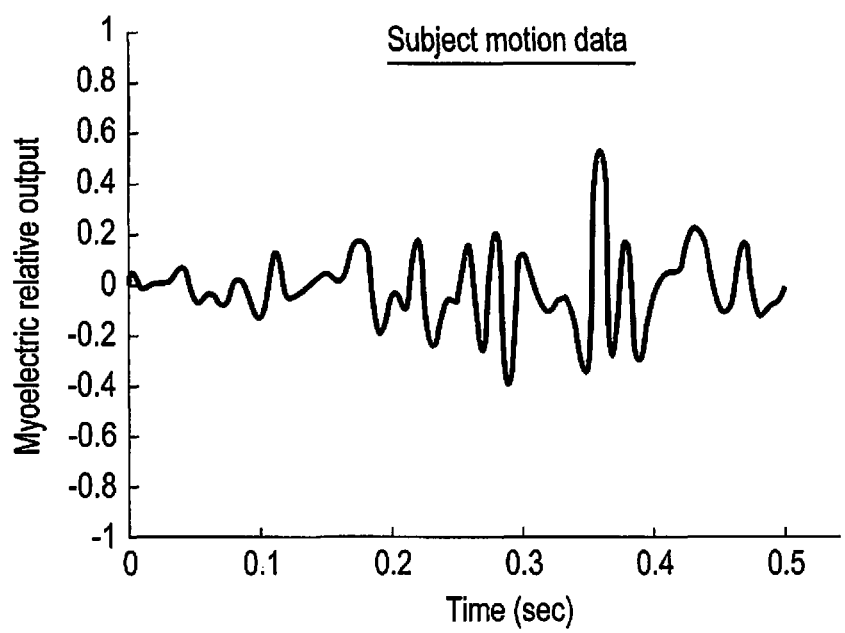
FIG. 4 shows an example of subject motion data according to the above embodiment.

The subject data acquisition module 101 acquires subject motion data and concomitant data associated with the subject motion data from the sensor devices 11a to 14a attached to the subject $U_L$. More specifically, the subject data acquisition module 101 acquires subject motion data with identification data that identifies that the subject motion data is from the sensor devices 11a to 14a attached to the subject $U_L$ and concomitant data accompanying the subject motion data. For example, in a case where the myoelectric sensor is attached to the right hand of the subject $U_L$, the subject data acquisition module 101 acquires, from the myoelectric sensor attached to the right hand of the subject $U_L$, time-series data of the quantity of activity of the right hand muscle (myoelectric relative output) as subject motion data as shown in FIG. 4.

In the above, while the case where the myoelectric sensor is attached to the right hand of the subject $U_L$, and the subject motion data and concomitant data is acquired from the myoelectric sensor are described, the subject motion data and concomitant data is acquired, in the same manner, from other sensor devices (for example, myoelectric sensors attached to the left hand and the abdomen, the pressure sensor or the like attached to the tool used by the subject $U_L$) worn by the subject $U_L$. At this time, it is preferable that the subject data acquisition module 101 acquires the subject motion data from each of the sensor devices 11a to 14a after synchronizing the timing of acquiring the subject motion data from each of the sensor devices 11a to 14a.

Figure 5:
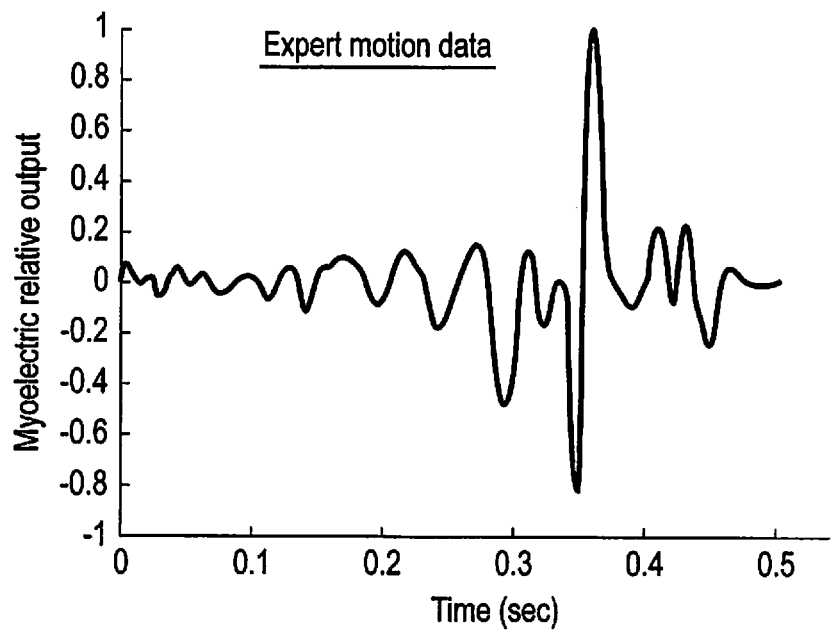
FIG. 5 shows an example of expert motion data according to the above embodiment.

As in the subject data acquisition module 101, the expert data acquisition module 102 acquires expert motion data (in other words, expert motion data without the above-mentioned identification data) and its concomitant data from the sensor devices 11b to 14b attached to the expert $U_H$. It is preferable that the expert data acquisition module 102 acquires the expert motion data from each of the sensor devices 11b to 14b after synchronizing the timing of acquiring the expert motion data from each of the sensor devices 11b to 14b. FIG. 5 shows an example of the time-series data of the quantity of activity of the right hand muscle acquired from the myoelectric sensor attached to the right hand of the expert $U_H$.

The motion data acquired by the subject data acquisition module 101 and the expert data acquisition module 102 and the concomitant data accompanying the motion data are output to the similarity determination module 103.

Upon receiving the subject motion data output from the subject data acquisition module 101 and the expert motion data output from the expert data acquisition module 102, the similarity determination module 103 compares the subject motion data and expert motion data having the same sensor type and attachment body part, which is indicated by the concomitant data which has been input together with these motion data and determines a similarity of these motion data.

Figure 6:
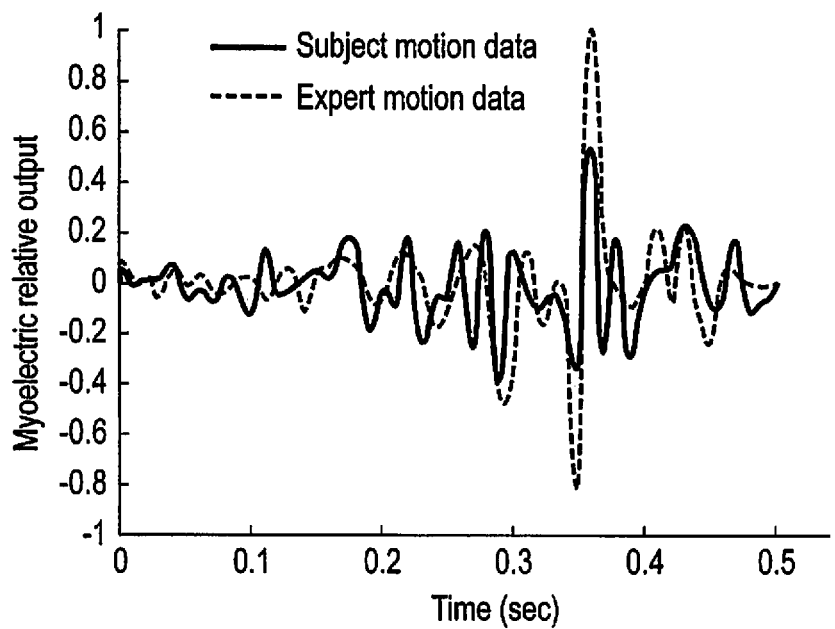
FIG. 6 is a diagram in which the subject motion data and the expert motion data according to the above embodiment is superimposed and compared.

More specifically, in a case where the motion data is time-series data as shown in FIGS. 4 and 5, the similarity determination module 103 superimposes the subject motion data and the expert motion data as shown in FIG. 6 to compares them, and determines the similarity of the subject motion data and the expert motion data by checking various items such as amplitude, frequency, phase, and displacement in order. For example, when checking the amplitude, the similarity determination module 103 determines whether a difference in the amplitude equal to or larger than a predetermined value is detected between the amplitude of the maximum peak of the subject motion data and the amplitude of the maximum peak of the expert motion data. Note that the predetermined value is preset for each item, and the similarity determination module 103 executes similar processing for each item.

Note that in order for the similarity determination module 103 to accurately superimpose the subject motion data and the expert motion data, it is necessary to synchronize the subject motion data and the expert motion data. A synchronization method includes a method of detecting sharp rising data edges that are common to the two motion data and adjusting the rising time positions. For example, in a case where one of the sensor devices is a three-axis acceleration sensor capable of acquiring three types of sensor signals (time-series signals in the x-, y-, and z-axis directions), the time when a value obtained by adding power of the three signals where the power can be calculated by raising the signal in a unit time to the power of 2 increases by a certain threshold value or more is assumed to be the rising time, and the two motion data is synchronized. This allows the subject motion data and the expert motion data which are measured at different times to be accurately superimposed.

As a result of the above-described determination, in a case where there is an item in which a difference equal to or greater than a predetermined value has been detected, the similarity determination module 103 determines that a motion which can be a target for improvement with respect to the subject $U_L$ is present. The similarity determination module 103 outputs to the motion improvement instruction selection module 104 the items in which the difference equal to or greater than the predetermined value has been detected, and determination result data (for example, [item] amplitude is [how much difference] small, [item] timing (phase) is [what kind of difference] early, or the like) indicating what kind of difference the difference is when the difference is based on the expert $U_H$. Note that in addition to the determination result data, the similarity determination module 103 outputs to the motion improvement instruction selection module 104 concomitant data (in other words, concomitant data acquired together with the motion data to be a target for comparison) accompanying the motion data that has been used at the time of the determination.

As a result of the above-described determination, in a case where a difference of more than a predetermined value is detected in a plurality of items, the similarity determination module 103 may output to the motion improvement instruction selection module 104 only the determination result data on the item with the largest difference, or a plurality of pieces of determination result data sequentially from the determination result data on the item with the largest difference. According to this output, it is possible to present a motion improvement instruction to the subject $U_L$ with respect to a motion which should be immediately improved. The similarity determination module 103 may output to the motion improvement instruction selection module 104 only the determination result data on the item with the smallest difference, or a plurality of pieces of determination result data sequentially from the determination result data on the item with the smallest difference. According to this output, it is possible to present the motion improvement instruction to the subject $U_L$ with respect to a motion which is easily improved.

In the above description, the description has been made supposing the motion data is time-series data. In a case where the motion data is not time-series data but one measured value, the similarity determination module 103 determines whether a motion that can be a target for improvement with respect to the subject $U_L$ is present by determining whether the measured value is equal to or more than a predetermined value.

Furthermore, in the present embodiment, the similarity determination module 103 detects a difference equal to or more than a predetermined value in the subject motion data and the expert motion data in order to present to the subject $U_L$ a motion that can be a target for improvement. However the embodiment is not limited to this. For example, the similarity determination module 103 may further detect a portion that matches between the subject motion data and the expert motion data in order to present a motion of the subject $U_L$ that does not need to be improved, that is, a motion to be continued as it is.

According to this, in addition to the motion that can be a target for improvement, the motion that should be continued can also be presented to the subject $U_L$, so that the subject $U_L$ can recognize not only the poor motion but also the good motion of himself, making it possible to have the effect of maintaining or improving motivation for improvement in the motion of subject $U_L$.

Before describing the motion improvement instruction selection module 104, the motion improvement instruction database 201 will be described.

As shown in FIG. 7, the motion improvement instruction database 201 stores motion improvement instruction data which associates the character string data output from the motion improvement instruction selection module 104 with the concomitant data and the determination result data input to the motion improvement instruction selection module 104.

For example, according to the motion improvement instruction data a1 in FIG. 7, in a case where it is indicated that the sensor type indicated by the concomitant data input to the motion improvement instruction selection module 104 is "myoelectric sensor", the attachment body part indicated by the concomitant data is "right hand", and "the amplitude is small" based on the determination result data input to the motion improvement instruction selection module 104, it is indicated that the character string data expressing "apply strength with your right hand" is preferable as character string data output from the motion improvement instruction selection module 104.

Although only the motion improvement instruction data a1 in FIG. 7 has been described as an example here, the same also applies to other motion improvement instruction data a2 to a4 shown in FIG. 7, so that a detailed description thereof will be omitted in the embodiment.

Further, in the present embodiment, the case where the motion improvement instruction data includes character string data as an output from the motion improvement instruction selection module 104 is exemplified. However, the present embodiment is not limited to this. Instead of the character string data, motion improvement instruction data may include, for example, audio data, image (video) data, or the like as an output from the motion improvement instruction selection module 104. Further, motion improvement instruction data may include motion signal for haptic feedback utilizing electricity, sound wave, mechanical force as an output from the motion improvement instruction selection module 104.

Upon receipt of the determination result data and the concomitant data output from the similarity determination module 103, the motion improvement instruction selection module 104 selects the preferable motion improvement instruction data from the motion improvement instruction database 201 based on the input determination result data and concomitant data, and acquires character string data included in the selected motion improvement instruction data. The acquired character string data is output to the presentation module 105.

Upon receiving the input of the character string data output from the motion improvement instruction selection module 104, the presentation module 105 displays the character string indicated by the input character string data on a display monitor provided in the information processing device 16, or on a display monitor connected to the information processing device 16, and presents to the subject $U_L$ the character string, that is, a motion improvement instruction.

Note that the presentation module 105 presents the motion improvement instruction to the subject $U_L$ each time it receives an input of character string data from the motion improvement instruction selection module 104. That is, the motion improvement instruction may be presented to the subject $U_L$ in real time, or the input character string data may be stored in a temporary memory (not shown), and the motion improvement instruction based on the character string data stored in the temporary memory may be collectively presented to the subject $U_L$ at a predetermined timing.

Next, with reference to the flowchart of FIG. 8, an example of motion improvement promotion processing implemented by the motion improvement promotion program having the above-described functional configuration will be described.

First, the subject data acquisition module 101 acquires subject motion data and concomitant data accompanying the subject motion data from each of the sensor devices 11a to 14a attached to the subject $U_L$ (step S1). Along with the process of step S1, the expert data acquisition module 102 acquires expert motion data and concomitant data accompanying the expert motion data from each of the sensor devices 11b to 14b attached to the expert $U_H$ (step S2).

Both of the motion data and concomitant data that have been acquired are output to the similarity determination module 103.

Subsequently, the similarity determination module 103 receives the input of the motion data and concomitant data output from the subject data acquisition module 101 and the expert data acquisition module 102. Then, the similarity determination module 103 sequentially compares the subject motion data and the expert motion data whose sensor type and attachment body part indicated by the input concomitant data are the same, and determines whether a motion that can be a target for improvement with respect to the subject $U_L$ is present (Step S3).

As a result of the determination in step S3, in a case where it is determined that there is no difference which is equal to or more than a predetermined value between any subject motion data and expert motion data, and no motion that can be a target for improvement with respect to the subject $U_L$ is present (NO in step S3), the process in step S3 ends.

On the other hand, as a result of the determination in step S3, in a case where it is determined that there is a difference which is equal to or more than a predetermined value between any subject motion data and expert motion data, and a motion that can be a target for improvement with respect to the subject $U_L$ is present (YES in step S3), the similarity determination module 103 outputs to the motion improvement instruction selection module 104 the determination result data indicating items for which a difference equal to or greater than a predetermined value is detected and what kind of difference the difference is when the difference is based on the expert $U_H$, and the subject motion data and concomitant data attached to the expert motion data (step S4).

Next, the motion improvement instruction selection module 104 receives the input of the determination result data and the concomitant data output from the similarity determination module 103. The motion improvement instruction selection module 104 selects and acquires the motion improvement instruction data including the content of the input concomitant data and the determination result data from the motion improvement instruction database 201 as preferable motion improvement instruction data, and outputs character string data included in the selected and acquired motion improvement instruction data to the presentation module 105 (step S5).

Thereafter, upon receiving the input of the character string data output from the motion improvement instruction selection module 104, the presentation module 105 displays and outputs the character string data on the display monitor (step S6), and the processing in step S6 ends.

The present embodiment is described supposing the subject $U_L$ and the expert $U_H$ perform the same predetermined operation at the same time. However, it may not be possible for the subject $U_L$ and the expert $U_H$ to perform the same predetermined operation at the same time. Even if the subject $U_L$ performs a predetermined operation, when there is no expert $U_H$ who performs the same predetermined operation at the same time, there is no input to the expert data acquisition module 102, and therefore the expert data acquisition module 102 cannot obtain a target for comparison to the subject motion data, and the disadvantage that the motion improvement instruction cannot be presented to the subject $U_L$ occurs.

Therefore, as shown in FIG. 9, instead of the expert data acquisition module 102, a motion database 202 for storing expert motion data in advance may be separately provided.

The motion database 202, as shown in FIG. 10, stores motion data with which expert motion data and concomitant data is associated. Note that the concomitant data in this case indicates the content (operation content) of a predetermined operation in addition to the above-mentioned sensor type and the attachment body part. For example, the motion data b1 in FIG. 10 includes "expert motion data 1" which is expert motion data when the expert $U_H$ wears "myoelectric sensor" on the "right hand" and performs "screw tightening".

Although only the motion data b1 in FIG. 10 has been described as an example here, the same also applies to other motion data b2 to b4 shown in FIG. 10, so that a detailed description thereof will be omitted in the embodiment.

As shown in FIG. 9, in a case where the motion database 202 is separately provided in place of the expert data acquisition module 102, the expert motion data is acquired from the motion database 202 by the similarity determination module 103. The function of the similarity determination module 103 when the motion database 202 is provided will be described below.

Upon receipt of the subject motion data and its concomitant data output from the subject data acquisition module 101, the similarity determination module 103 acquires the expert motion data from the motion database 202 based on the input concomitant data. Specifically, the similarity determination module 103 obtains, from the motion database 202, expert motion data associated with the sensor type, the attachment body part, and the operation content indicated by the input concomitant data.

As described above, the configuration is such that the motion database 202 is separately provided in place of the expert data acquisition module 102, and the similarity determination module 103 can acquire expert motion data from the motion database 202, so that even when there is no expert $U_H$ when the subject $U_L$ performs the predetermined operation, it is possible to present a preferable motion improvement instruction to the subject $U_L$.

On the other hand, in a case where the motion database 202 is additionally provided as described above and one piece of expert motion data to be a model is stored in the motion database 202 in association with the sensor type, the attachment body part, and the operation content, the following disadvantage may occur.

For example, in a case where the subject $U_L$ is a beginner having a very low proficiency level in a predetermined operation, the expert motion data stored in the above-described motion database 202 may cause a lot of motions that can be targets for improvement to be detected since there is a large deviation in proficiency level. In this case, too many motion improvement instructions are presented to the subject $U_L$. Thus the disadvantage that the subject $U_L$ is confused on the contrary can occur.

In order to solve this disadvantage, the motion data stored in the motion database 202 may have a data structure as shown in FIG. 11, and a proficiency level acquisition module 106 as shown in FIG. 12 may be added to the function module implemented by the motion improvement promotion program.

FIG. 11 is a diagram showing an example of a data structure of motion data stored in the motion database 202. Unlike the motion data shown in FIG. 10, the motion data shown in FIG. 11 is associated further with the proficiency level data in addition to the expert motion data and concomitant data. The proficiency level data indicates the proficiency level of the subject $U_L$ to the operation content indicated by the associated concomitant data. In this case, the proficiency level is a value by the N-level evaluation with a level from 1 to N, and the larger the value, the higher the proficiency level.

For example, the motion data c1 in FIG. 11 is expert motion data when the expert $U_H$ wears "myoelectric sensor" on the "right hand" and performs "screw tightening", and is "expert motion data 1a" for subject $U_L$ whose proficiency level is "3". On the other hand, while as in the motion data c1, the motion data c2 in FIG. 10 is expert motion data when the expert $U_H$ wears "myoelectric sensor" on the "right hand" and performs "screw tightening", it is "expert motion data 1b" for subject $U_L$ whose proficiency level is "2"

Although only the motion data c1, c2 in FIG. 11 has been described as an example here, the same also applies to other motion data c3, c4 shown in FIG. 11, so that a detailed description thereof will be omitted in the embodiment.

The proficiency level acquisition module 106 has a function of acquiring proficiency level data indicating the proficiency level of the subject $U_L$ and outputting it to the similarity determination module 103. The proficiency level data may be acquired (input) from an external device possessed by a supervisor at the site where the subject $U_L$ performs an operation, or may be generated as analysis results after analyzing the subject motion data acquired by the subject data acquisition module 101.

In this case, when the similarity determination module 103 receives the subject motion data and its concomitant data output from the subject data acquisition module 101, and the proficiency level data output from the proficiency level acquisition module 106, the similarity determination module 103 acquires preferable expert motion data from the motion database 202 based on the concomitant data and the proficiency level data that have been input. Specifically, the similarity determination module 103 acquires the expert motion data in the motion data including the sensor type, the attachment body part and the operation content that are indicated by the concomitant data, and the proficiency level indicated by the proficiency level data from the motion database 202.

In this case, the similarity determination module 103 acquires the expert motion data in the motion data including the proficiency level indicated by the acquired proficiency level data. However the present embodiment is not limited to this. The similarity determination module 103 may acquire the expert motion data in the motion data including the proficiency level which is one level higher than the proficiency level indicated by the acquired proficiency level data.

In addition to the character string data from the motion improvement instruction selection module 104, the presentation module 105 may present a character string indicating that "proficiency level improves by one level" by executing the motion improvement instruction indicated by the character string data, or may present character string data indicating that "the operation time of a predetermined operation is shortened by M seconds" by executing the motion improvement instruction indicated by the character string data. Note that the value of M corresponds to a difference between the time required for the expert $U_H$ to perform a predetermined operation where the time is obtained by analyzing the expert motion data of the proficiency level which is one level higher than the master level indicated by the proficiency level data input to the similarity determination module 103, and the time required for the subject $U_L$ to perform a predetermined operation where the time is obtained by analyzing the subject motion data input to the similarity determination module 103.

As described above, even with the same operation content, the configuration is such that the motion database 202 for storing expert motion data which is graded for each proficiency level is provided, and the similarity determination module 103 can obtain expert motion data suitable for the proficiency level of the subject $U_L$ from the motion database 202, so that it is possible to prevent the expert motion data whose the proficiency level greatly deviates from that of the subject motion data from being a target for comparison to the subject motion data and it is possible to achieve gradual improvement in proficiency level of the subject $U_L$.

In the above example, the case where expert motion data preferable for the subject $U_L$ is selected according to the proficiency level is exemplified. However, the present embodiment is not limited to this embodiment. For example, preferable expert motion data may be selected according to gender, age, height, weight, years of work engagement, and the like.

According to the first embodiment described above, the information processing device 16 determines the similarity between the subject $U_L$ and the expert $U_H$ with respect to the operation at the time of the predetermined operation. The information processing device 16 presents the preferable motion improvement instruction to the subject $U_L$. That is, it is possible to expect to improve the efficiency of motion training and to shorten necessary technical acquisition.

Second Embodiment

Next, a second embodiment will be described. In the present embodiment, a case where the motion improvement promotion program shown in FIG. 3 is further provided with a motion estimation module 107 shown in FIG. 13 will be described. In the following description, attention is focused mainly on the difference from the first embodiment, and the same configuration is denoted by the same reference numeral and the description may be omitted. In addition, in the present embodiment, concomitant data indicates a sensor type, an attachment body part, and operation content.

Figure 13:
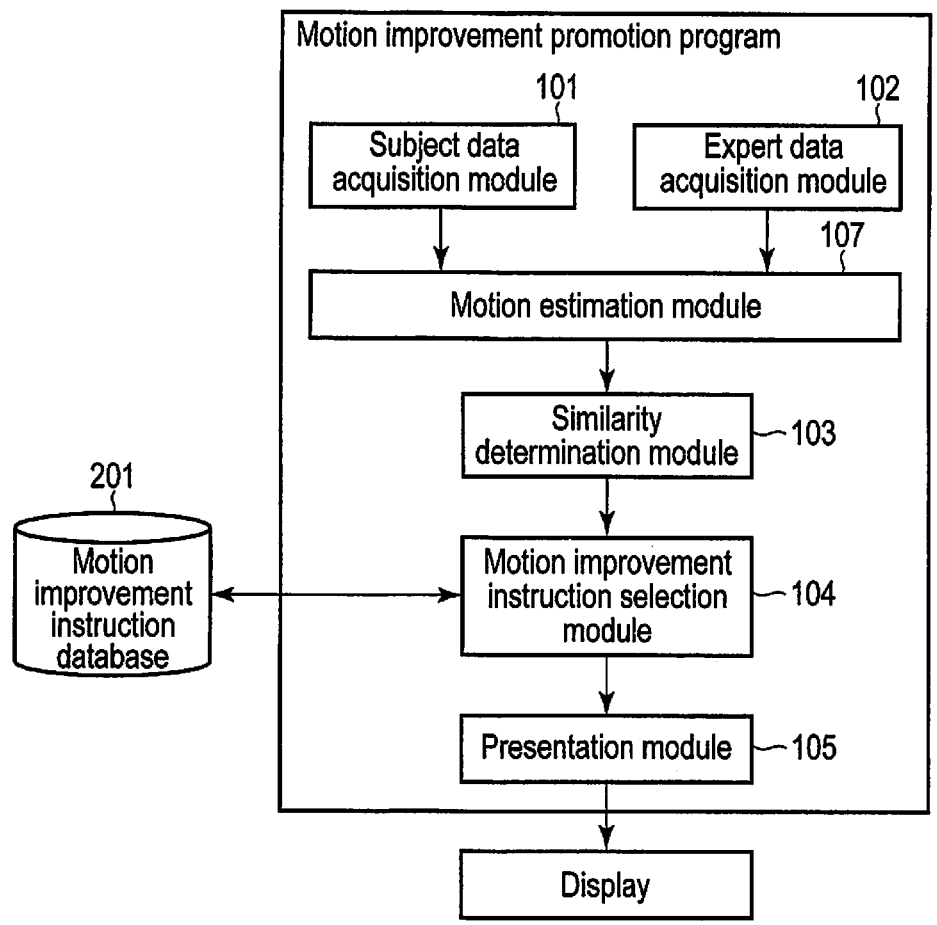
FIG. 13 is a block diagram showing an example of a functional configuration of a motion improvement promotion program according to a second embodiment.

FIG. 13 is a block diagram showing an example of a functional configuration of a motion improvement promotion program according to a second embodiment.

Upon receipt of the subject motion data and concomitant data output from a subject data acquisition module 101, a motion estimation module 107 extracts a feature quantity from the subject motion data. The motion estimation module 107 estimates the motion of the subject $U_L$ based on this feature quantity by machine learning/determination analysis such as a known neural network, SVM (Support Vector Machine), random forest, or the like using the learning result which the motion estimation module 107 has learned beforehand.

For example, it is assumed that the sensor type indicated by the input concomitant data is "myoelectric sensor", the attachment body part indicated by the input concomitant data is "right hand" and the operation content indicated by the input concomitant data is "screw tightening". In this case, the motion estimation module 107 extracts the feature quantity from the input subject motion data and, based on this feature quantity, determines which the motion of the subject $U_L$ corresponds to, "grips", "releases", or "twist", using the learning dictionary which the motion estimation module 107 has learned beforehand. Thereby, the estimation module 107 estimates the motion of the subject $U_L$.

Figure 14:
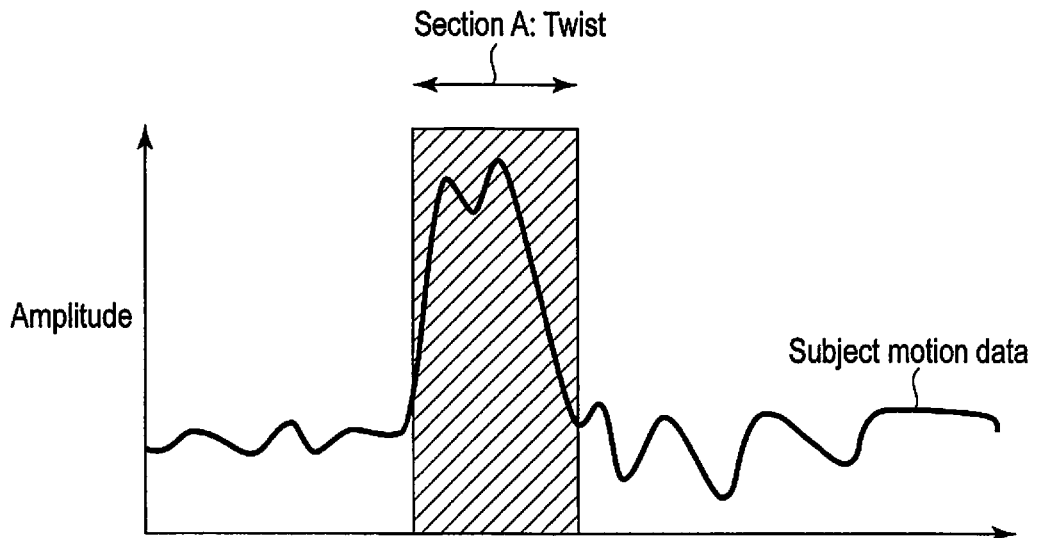
FIG. 14 shows an example of the subject motion data according to the above embodiment.

The motion estimation module 107 outputs the subject motion data to a similarity determination module 103 after adding (labeling) the estimation result data indicating the motion type of the subject $U_L$ to the input subject motion data. For example, it is assumed that the motion estimation module 107 estimates that the motion of the subject $U_L$ in the section A of the subject motion data shown in FIG. 14 is "twisting". In this case, the motion estimation module 107 outputs the subject motion data to the similarity determination module 103 after labeling so as to indicate that the motion of the subject $U_L$ in the section A is "twisting".

Note that the motion estimation module 107 executes similar processing on the expert motion data output from an expert data acquisition module 102 and outputs the expert motion data to the similarity determination module 103 after labeling the estimation result data indicating the motion type of the expert $U_H$ to input expert motion data.

The subject motion data and the expert motion data are labeled to indicate the motion type of the subject $U_L$ and the expert $U_H$ by the motion estimation module 107, so that the following advantages can be obtained.

In a case where the subject motion data and the expert motion data are time-series data, the similarity determination module 103 superimposes and compares these motion data, and determines the similarity of these motion data. However, since there is a gap in the occurrence time of the motion to be compared between the subject motion data and the expert motion data, there is a disadvantage that it is impossible to superimpose and compare these motion data as they are. Therefore, it is necessary to perform processes in which the timing at which the subject data acquisition module 101 acquires the subject motion data and the timing at which the expert data acquisition module 102 acquires the expert motion data are synchronized in advance, and heads of the acquired subject motion data and the expert motion data are aligned.

Figure 15:
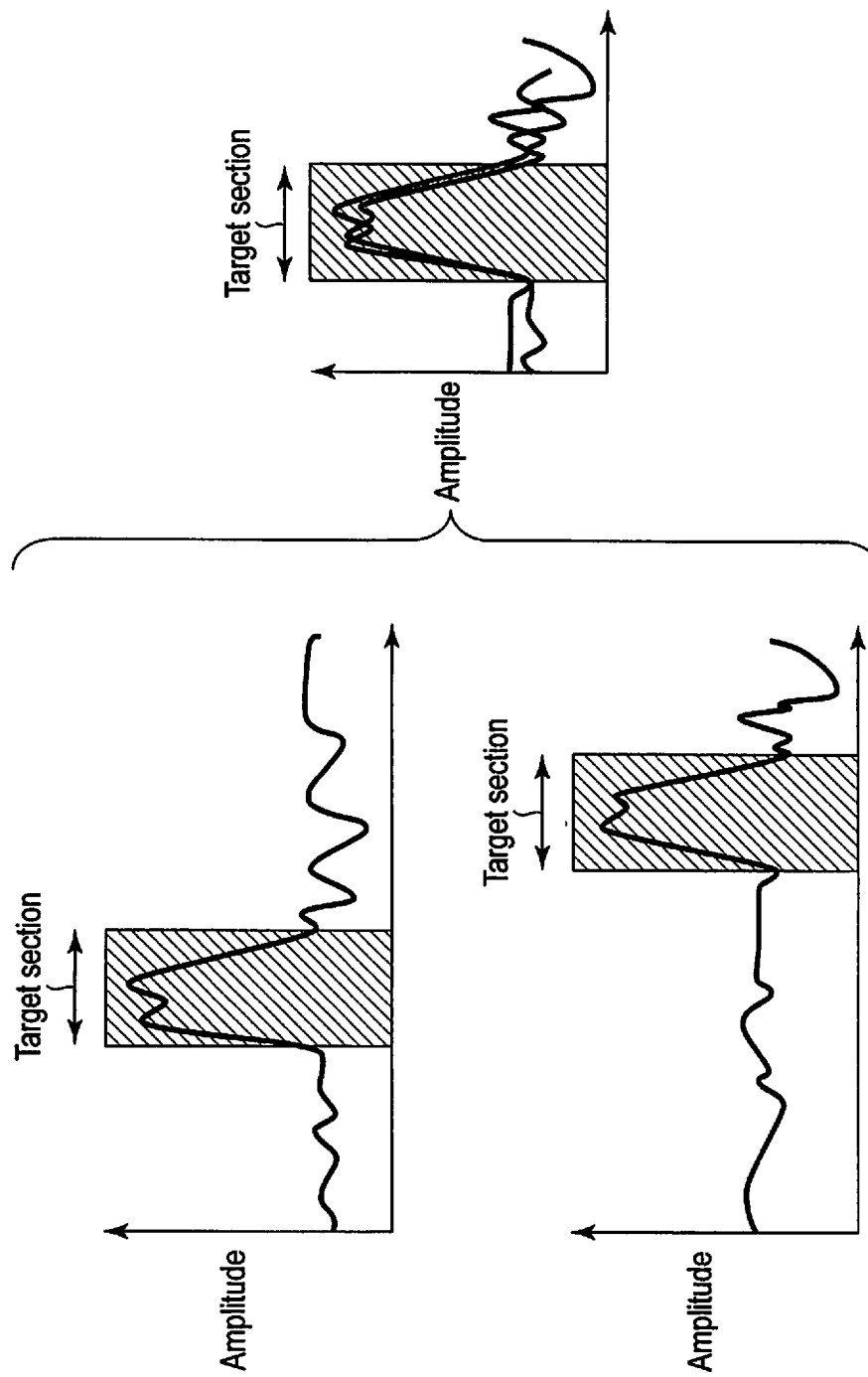
FIG. 15 is a diagram in which the subject motion data and the expert motion data according to the above embodiment are superimposed and compared.

On the other hand, the subject motion data and the expert motion data are labeled to indicate the motion type of the subject $U_L$ and the expert $U_H$ by the motion estimation module 107, whereby, as shown in FIG. 15, for example, even if a gap is present in an occurrence time between motions to be compared, it is possible to extract only the sections to be compared and easily compare them.

In the first embodiment described above, the case where the more preferable motion improvement instruction data is selected and acquired from the motion improvement instruction database 201 by the motion improvement instruction selection module 104, and a motion improvement instruction to the subject $U_L$ is uniquely determined are exemplified. Use of the estimation result data by the motion estimation module 107 makes it possible to present the more detailed motion improvement instruction to the subject $U_L$.

Figures 16, 17:
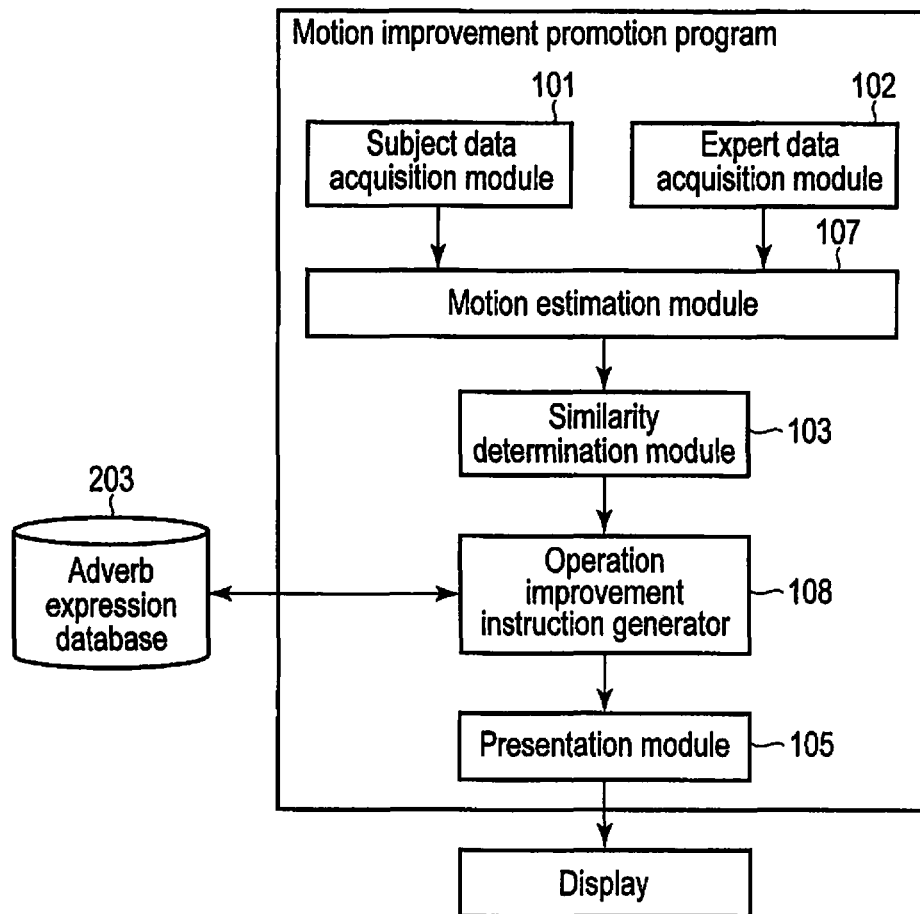
FIG. 16 shows an example of a functional configuration of a motion improvement promotion program different from that in FIG. 13.
FIG. 17 shows an example of a data structure of adverb expression data according to the above embodiment.

In this case, as shown in FIG. 16, an adverb expression database 203 is provided in place of the motion improvement instruction database 201 shown in FIG. 13, and a motion improvement instruction generator 108 is provided as a function module in place of the motion improvement instruction selection module 104.

As shown in FIG. 17, the adverb expression database 203 stores adverb expression data in which (part of) concomitant data, determination result data, estimation result data, and adverb expression are associated with each other. For example, according to the adverb expression data d1 in FIG. 17, in a case where the sensor type indicated by the concomitant data is "myoelectric sensor", the attachment body part indicated by the concomitant data is "right hand", the determination result data indicates "amplitude is small", and the motion type indicated by the estimation result data is "grip", it is indicated that the adverb expression is "strongly". In addition, according to the adverb expression data d2 in FIG. 17, in a case where the sensor type indicated by the concomitant data is "myoelectric sensor", the attachment body part indicated by the concomitant data is "right hand", the determination result data indicates "timing is early", and the motion type indicated by the estimation result data is "twist", it is indicated that the adverb expression is "slowly".

When the motion improvement instruction generator 108 shown in FIG. 16 receives the determination result data and the concomitant data output from the similarity determination module 103, and the estimation result data added to the motion data used at the time of determination by the similarity determination module 103 (in other words, the estimation result data added to the motion data to be a target for comparison), the motion improvement instruction generator 108 generates a motion improvement instruction based on each input data and the adverb expression database 203.

More specifically, as shown in FIG. 18(*a*), the motion improvement instruction generator 108 recognizes the attachment body part indicated by the input concomitant data as a body part which is a target for improvement. In addition, as shown in FIG. 18(*b*), the motion improvement instruction generator 108 recognizes the motion type indicated by the input estimation result data as a motion which is a target for improvement. Further, as shown in FIG. 18(*c*), based on the input concomitant data, the determination result data and the estimation result data, the motion improvement instruction generator 108 selects and acquires preferable adverb expression data from the adverb expression database 203. The motion improvement instruction generator 108 determines the adverb expression to be added to the motion improvement instruction to be presented to the subject $U_L$.

In accordance with preset logic, the motion improvement instruction generator 108 generates the motion improvement instruction by combining the body part to be a recognized/ determined target for improvement, the motion to be a target for improvement, and the adverb expression. Specifically, the motion improvement instruction generator 108 generates the motion improvement instruction according to the logic of "please do [action] [body part] [adverb expression]".

For example, it is assumed that the sensor type indicated by the concomitant data is "myoelectric sensor", the attachment body part indicated by the concomitant data is "right hand", the input determination result data indicates "amplitude is small", the motion type indicated by the estimation result data is "grip", and the preferable adverb expression is "strongly". In this case, the motion improvement instruction generator 108 generates the motion improvement instruction of "[grip] [right hand] [strongly]". The motion improvement instruction data indicating the generated motion improvement instruction is output to a presentation module 105 and presented to the subject $U_L$ by the presentation module 105.

Note that stepwise adverb expressions may be used for the motion improvement instruction generated by the motion improvement instruction generator 108. Specifically, stepwise adverb expressions such as "very strongly" or "somewhat strongly" may be used in addition to adverb expressions "strongly".

In this case, the similarity determination module 103 does not simply determine whether there is a difference equal to or more than a predetermined value between the subject motion data and the expert motion data, but instead makes a determination based on the threshold value set stepwise. For example, when the first threshold value and the second threshold value (where the first threshold value<the second threshold value) are set as the stepwise threshold values, the similarity determination module 103 determines whether there is a difference equal to or larger than the first threshold value and smaller than the second threshold value between the subject motion data and the expert motion data, or whether there is a difference equal to or larger than the second threshold value. For example, when the subject motion data is smaller in amplitude than the expert motion data, and the difference is equal to or larger than the first threshold value and smaller than the second threshold value, the similarity determination module 103 outputs the determination result indicating "amplitude is small". Also, when the subject motion data is smaller in amplitude than the expert motion data, and when the difference is equal to or larger than the second threshold value, the similarity determination module 103 outputs determination result data indicating "amplitude is very small".

Since the determination result data becomes elaborate in this manner, it becomes possible to subdivide the adverb expression data stored in the adverb expression database 203 (for example, determination result data of "amplitude is small" is associated with the adverb expression of "strongly", and the adverb expression of "amplitude is very small" is associated with the adverb expression of "very strongly", or the like), consequently, the motion improvement instruction generator 108 can generate the motion improvement instruction using a stepwise adverb expression.

According to the second embodiment described above, the information processing device 16 further includes the motion estimation module 107. The motion estimation module 107 estimates the operation type of the subject $U_L$ and the expert $U_H$, and labels subject motion data and expert motion data with estimation result data indicating the estimated motion type. Therefore, it is possible to easily compare the subject motion data with the expert motion data and to present the more detailed motion improvement instruction to the subject $U_L$.

According to at least one of the embodiments described above, it is possible to provide the information processing device, the method, and the program capable of promoting the training of an operator (subject $U_L$).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information processing device comprising:
a memory; and
a hardware processor in communication with the memory, the hardware processor configured to:
acquire a first motion data indicating a motion of a first operator, the first motion data comprising a first time series;
acquire a second motion data indicating a motion of a second operator, the second motion data comprising a second time series;
synchronize the first motion data and the second motion data by detecting sharp rising data edges that are common to the first and second time series and adjusting rising time positions;

compare the first motion data and the second motion data;
determine a similarity of the first motion data and the second motion data; and
present to the first operator instruction data indicating an improvement point relating to a motion at a time of performing a predetermined operation in accordance with a determination result,
wherein the first motion data and the second motion data are acquired from one or more motion sensors attached to one or more tools.

2. The information processing device of claim 1, wherein the hardware processor is further configured to select instruction data to be presented to the first operator from a first storage storing a plurality of instruction data in accordance with the determination result.

3. The information processing device of claim 1,
wherein the first motion data is data indicating a motion when the first operator performs the predetermined operation, and
wherein the second motion data is data indicating a motion when the second operator having a higher proficiency level than the first operator performs the predetermined operation.

4. The information processing device of claim 2,
wherein the first motion data is data indicating a motion when the first operator performs the predetermined operation, and
wherein the second motion data is data indicating a motion when the second operator having a higher proficiency level than the first operator performs the predetermined operation.

5. The information processing device of claim 2, further comprising the first storage.

6. The information processing device of claim 2, wherein the hardware processor is configured to:
acquire the first motion data measured by a first sensor device capable of measuring the first motion data, and concomitant data indicating at least a type of the first sensor device and a measurement body part;
acquire the second motion data measured by a second sensor device, and concomitant data;
compare the first motion data and the second motion data;
detect a difference between the first motion data and the second motion data;
determine a similarity of the first motion data and the second motion data; and
output a result of the determination as a determination result data,
wherein the second sensor device is a sensor device whose measurement body part is the same as a measurement body part of the first motion data, and which type is the same as a type of the first sensor device.

7. The information processing device of claim 6,
wherein the first storage is configured to store instruction data in which at least the concomitant data, the determination result data, and a motion improvement instruction for the first operator are associated with each other, and
wherein the hardware processor is configured to select the instruction data including determination result data on the difference and the concomitant data acquired together with first motion data which is a target for comparison when detecting the difference, as instruction data to be presented to the first operator, if the detected difference is equal to or greater than a predetermined value.

8. The information processing device of claim 6,
wherein the concomitant data further indicates a content of the predetermined operation in addition to the type of the sensor device and the measurement body part,
wherein the information processing device further comprises a second storage configured to store the concomitant data and the second motion data in association with each other, and
wherein the hardware processor is configured to obtain second motion data associated with the concomitant data acquired together with the first motion data from the second storage as a target for comparison to the first motion data.

9. The information processing device of claim 8,
wherein the second storage is further configured to store proficiency level data in addition to the concomitant data and the second motion data, the proficiency level data, the concomitant data and the second motion data being associated with each other, the proficiency level data indicates a proficiency level of the first operator with respect to the predetermined operation,
wherein the hardware processor is further configured to:
acquire the proficiency level data; and
acquire the concomitant data acquired together with the first motion data, and second motion data associated with the acquired proficiency level data from the second storage as a target for comparison to the first motion data.

10. The information processing device of claim 6, wherein the hardware processor is further configured to:
analyze each of the first motion data and the second motion data;
estimate respective types of one or more motions by the first operator and the second operator indicated by the first motion data and the second motion data;
add estimation result data capable of identifying the estimated type of motions to the respective motion data; and
extract respective portions to which the estimation result data indicating the same type of motions is added from the first motion data and the second motion data to compare the first motion data and the second motion data.

11. The information processing device of claim 10, wherein the hardware processor is further configured to:
generate a motion improvement instruction for the first operator in accordance with a result of a determination; and
set the motion improvement instruction as instruction data,
wherein the information processing device further comprises a third storage configured to store a plurality of adverb expression data in which an adverb expression included in the generated motion improvement instruction, the determination result data, the concomitant data, and the estimation result data are associated with each other.

12. The information processing device of claim 11, wherein the hardware processor is configured to:
acquire adverb expression data comprising a determination result data relating to the detected difference, concomitant data acquired together with first motion data which is a target for comparison when detecting the difference, and estimation result data added to the first motion data which is the target for comparison; and
generate a motion improvement instruction by combining an attachment body part indicated by the concomitant data, a type of motion indicated by the estimation result data, and an adverb expression indicated by the acquired adverb expression data.

13. The information processing device of claim 1, further comprising a display that displays the instruction data.

14. The processing device of claim 1, wherein the one or more motion sensors are myoelectric sensors.

15. The processing device of claim 1, wherein the instruction data comprise character string data specifying a recommendation for applied strength.

16. The processing device of claim 1, wherein determining the similarity of the first motion and the second motion comprises determining whether a difference in amplitude and a difference in timing between motions are above predetermined values.

17. The device according to claim 1, wherein comparing the first motion data and the second motion data comprises comparing sections of the first time series and the second time series with matching motion types.

18. The device according to claim 1, wherein the motion data corresponds to a motion comprising at least one of: twisting, grasping, gripping, releasing, and screw tightening.

19. A method comprising:
    acquiring a first motion data indicating a motion of a first operator, the first motion data comprising a first time series;
    acquiring a second motion data indicating a motion of a second operator, the second motion data comprising a second time series;
    synchronizing the first motion data and the second motion data by detecting sharp rising data edges that are common to the first and second time series and adjusting rising time positions;
    comparing the first motion data and the second motion data and determining a similarity of the first motion data and the second motion data; and
    presenting to the first operator instruction data indicating an improvement point relating to a motion at a time of performing a predetermined operation in accordance with a determination result,
    wherein the first motion data and the second motion data are acquired from one or more motion sensors attached to one or more tools.

20. A non-transitory computer-readable storage medium storing instructions executed by a computer, wherein the instructions, when executed by the computer, cause the computer to perform:
    acquiring a first motion data indicating a motion of a first operator, the first motion data comprising a first time series;
    acquiring a second motion data indicating a motion of a second operator, the second motion data comprising a second time series;
    synchronizing the first motion data and the second motion data by detecting sharp rising data edges that are common to the first and second time series and adjusting rising time positions;
    comparing the first motion data and the second motion data and determining a similarity of the first motion data and the second motion data; and
    presenting to the first operator instruction data indicating an improvement point relating to a motion at a time of performing a predetermined operation in accordance with a determination result,
    wherein the first motion data and the second motion data are acquired from one or more motion sensors attached to one or more tools.

* * * * *